United States Patent [19]  [11] 4,358,530
Shiba  [45] Nov. 9, 1982

[54] PHOTOSENSITIVE LITHOGRAPHIC PRINTING PLATE PRECURSOR AND A METHOD FOR PREPARING A PRINTING PLATE THEREFROM

[75] Inventor: Keisuke Shiba, Shizuoka, Japan

[73] Assignee: Fuji Photo Film Co., Ltd., Kanagawa, Japan

[21] Appl. No.: 193,319

[22] Filed: Oct. 2, 1980

[30] Foreign Application Priority Data

Oct. 2, 1979 [JP] Japan ................. 54/126970

[51] Int. Cl.$^3$ ................. G03T 7/02; G03C 1/73
[52] U.S. Cl. ................. 430/273; 430/156; 430/302; 430/271; 430/949; 430/502; 430/564; 430/599; 430/278
[58] Field of Search ............. 430/273, 271, 156, 302, 430/306, 502, 564, 599, 949, 278

[56] References Cited

U.S. PATENT DOCUMENTS

| | | | |
|---|---|---|---|
| 4,168,977 | 9/1979 | Takada et al. | 430/564 |
| 4,188,215 | 2/1980 | Sato et al. | 430/156 |
| 4,221,857 | 9/1980 | Okutsu et al. | 430/599 |

FOREIGN PATENT DOCUMENTS 2030309 4/1980 United Kingdom.

Primary Examiner—Won H. Louie, Jr.
Attorney, Agent, or Firm—Sughrue, Mion, Zinn, Macpeak & Seas

[57] ABSTRACT

A photosensitive lithographic printing plate precursor and a method for the preparation of a lithographic printing plate is described, said precursor comprising a support, a non-silver photosensitive layer and a photographic silver halide emulsion coating, and exhibiting photographic camera speed and a printing durability equivalent to the conventional type presensitized plate due to the underlying non-silver photosensitive layer; the silver halide emulsion coating contains a compound represented by the formual (I)

$$R^1NHNHCOR^2 \qquad (I)$$

in which $R^1$ represents an aryl group and $R^2$ represents hydrogen, an aryl group, or an aliphatic group.

26 Claims, No Drawings

PHOTOSENSITIVE LITHOGRAPHIC PRINTING PLATE PRECURSOR AND A METHOD FOR PREPARING A PRINTING PLATE THEREFROM

BACKGROUND OF THE INVENTION

1. Field of the Invention

This invention relates to a photosensitive lithographic printing plate precursor having an ultra-high photographic speed, an excellent ink receptivity, a good tonal reproduction and a high printing durability and a method of producing a printing plate therefrom, and in particular to a pre-sensitized plate (referred to hereinafter as a PS plate) based on the photosensitivity of silver halide and a method for preparing a printing plate therefrom.

2. Description of the Prior Art

Various types of PS plates utilizing the photosensitivity of silver halide have been described in the art, for example, in Japanese Patent Publication Nos. 27242/69, 16725/73, and 30562/73, British Pat. No. 1,567,844, U.S. Pat. Nos. 4,173,477, 3,083,097, 3,161,508, 3,721,559 and 3,146,104, etc. Such plates, however, exhibit defects such as low printing durability, a tendency to generate stain, or poor oleophilicity at image areas. In order to eliminate such deficiencies, other types of high-speed PS plates have been proposed in which a silver halide photographic emulsion coating is provided on the surface of a conventional PS plate having a non-silver photosensitive layer. Such plates are disclosed, for example, in Japanese Patent Publication No. 26521/71, Japanese Patent Application (OPI) No. 27804/79 (the term "OPI" as used herein refers to a "published unexamined Japanese patent application"), German Patent Application (OLS) Nos. 2,517,711, 2,640,763, etc. Other improved types of plates are described in, for example, U.S. Pat. No. 3,245,793, U.S. Defensive Publication No. T870,022, Japanese Patent Publication No. 23721/72, etc., in which an intermediate layer is present between the non-silver photosensitive layer and the silver halide containing photographic coating. Provision of such an intermediate layer, however, raises the manufacturing cost, and further suffers from a poor printing durability and oleophilicity in comparison to the one without such an intermediate layer. Moreover, when the thickness of the intermediate layer exceeds about one micron, the reproducibility of the image forming behavior deteriorates. To overcome this defect, still other types of PS plates have been disclosed in Japanese Patent Application (OPI) Nos. 74258/79, 76162/79 and 100596/79. Unfortunately, these types of plates still exhibit many drawbacks; as TAGA Proceedings pointed out (1975, pp. 1–22), when such a high-speed PS plate can be used for projection plate making, the fidelity of the reproduced image drastically deteriorates with the increase of magnification ratio when the original contains a very fine image or halftone images with a high dot density. The increase of the magnification ratio also causes the tonal range of a screened image to shrink.

SUMMARY OF THE INVENTION

An object of the present invention is to provide a PS plate which overcomes such defects, and a method of printing plate preparation therewith. Thus, a primary object of the present invention is to provide a PS plate for use in projection plate making exhibiting excellent fundamental printing characteristics, such as durability, a high degree of oleophilicity in image areas, resistance to stain formation at non-image areas, etc., and having an increased photographic speed of from about 25 to $10^5$ times as high as that of the conventional types of PS plate.

A second object of the present invention is to provide a PS plate which can reproduce an image with an acceptably high fidelity not only under a one-to-one size projection, but also under a high magnification ratio projection ranging from about two-to-one to ten-to-one times.

A third object of the present invention is to provide a method for printing plate preparation which can be readily, rapidly, and stably accomplished with an automatic processor.

Still other objects will become evident from the following detailed description.

The above-cited and additional objects of the present invention have been achieved by devising a new PS plate structure, comprising, in sequence, a support having a hydrophilic surface (e.g., an aluminum sheet), a non-silver photosensitive layer capable of providing an oleophilic image, and a photosensitive silver halide photographic emulsion coating in which the silver halide grains have an average diameter not exceeding about 0.7 microns and which contains a compound represented by the formula (I)

$$R^1NHNHCOR^2 \qquad (I)$$

wherein $R^1$ represents an aryl group, and $R^2$ hydrogen, an aryl group, or an aliphatic group, and, more preferably, also comprises a poly(alkylene oxide) or a derivative therefrom having a molecular weight of at least 600, the coating coverage (after drying) of said silver halide emulsion being from 1 to 10 g/m$^2$, in which the coating density for silver is from 9 millimol/m$^2$ to 33 millimol/m$^2$.

A method of preparation of a printing plate is also disclosed, starting with a PS plate as described above, said method comprising (a) imagewise exposure, (b) development with a developer containing a dihydroxybenzene reducing agent and a free sulfite ion at a concentration of at least 0.18 mol/l, (c) fixing the developed photographic coating, (d) uniformly exposing the thus-processed plate with radiation active to said non-silver photosensitive layer, (e) washing to remove said silver halide emulsion coating, and (f) a second development, with a second developer, to develop said non-silver photosensitive layer.

DETAILED DESCRIPTION OF THE INVENTION

In order to achieve all of the cited objects simultaneously, extensive research was conducted on the interaction between the non-silver photosensitive layer and the silver halide emulsion coating, particularly the relationship between the silver image formed in the silver halide emulsion coating and the final oleophilic image provided with the non-silver photosensitive layer, and further on the nature of the image area of the resulting printing plate. As a result of such research, it has been found that, with the particular combination of certain types of non-silver photosensitive layer and of silver halide emulsion coating, in accordance with the present invention, an unexpected excellent sharp cut image about a halftone dots and line image can be obtained. Such an advantageous phenomenon has been found to occur when the concentration of the sulfite ion in the first developer exceeds a certain value. This effect appears intensely for the photographic silver halide emulsion coating of the present invention (compared to conventional type emulsions), and, in particular, for the oleophilic image provided with the non-silver photosensitive layer of the present invention. It has further been found that a high concentration of sulfite ion in the first developer (viz., at least 0.18 mol/l) enables stable and rapid processing, moreover saving the amount of silver halide required.

The components of the photosensitive lithographic printing plate precursor of this invention are described hereinafter. Any support for a lithographic printing plate can be used in this invention provided that it has a hydrophilic surface. Suitable supports include paper, plastics (e.g., polyethylene, polypropylene, and polystyrene) laminated paper, plates of metals such as aluminum (including aluminum alloys), zinc, iron and copper, films of plastics such as cellulose diacetate, cellulose triacetate, cellulose propionate, cellulose butyrate, cellulose butyrate acetate, cellulose nitrate, polyethylene terephthalate, polyethylene, polystyrene, polypropylene, polycarbonate, and polyvinyl acetal, and paper or plastic films laminated or metallized with the above-identified metals. An aluminum plate or a composite sheet wherein an aluminum sheet is combined with a plastic film is preferably used.

To provide a hydrophilic surface, these supports are optionally subjected to a surface treatment or other treatments to provide a hydrophilic layer. Various methods are known to render the surface of the support hydrophilic. Methods applicable to a support having a plastic surface include various surface treatments, such as chemical treatment, discharge treatment, flame treatment, ultraviolet treatment, high frequency treatment, glow discharge treatment, active plasma treatment and laser treatment, as described, for example, in U.S. Pat. Nos. 2,764,520, 3,497,407, 3,145,242, 3,376,208, 3,072,483, 3,475,193, 3,360,448, and British Pat. No. 788,365. If necessary, these surface treatments may be followed by the provision of a hydrophilic layer, as described in U.S. Patent 2,649,373, Japanese Patent Application (OPI) Nos. 40890/78 and 61643/78.

Surface treatments preferably applied to a support having an aluminum surface include surface treatments such as graining, immersion in an aqueous solution of sodium silicate, potassium fluorozirconate, and phosphate salt, and anodization. An aluminum plate which is, as described in U.S. Pat. No. 2,714,066, immersed in an aqueous solution of sodium silicate after graining, and an aluminum plate which is, as described in U.S. Pat. No. 3,181,461, immersed in an aqueous solution of an alkali metal silicate after anodization are used with advantage. The above anodization treatment can be carried out by passing an electric current through an aluminum anode in an electrolyte comprising one or more aqueous or non-aqueous solutions of inorganic acids such as phosphoric acid, chromic acid, sulfuric acid, boric acid, or organic acids such as oxalic acid, sulfamic acid, or salts thereof, preferably in an electrolyte composed of phosphoric acid, sulfuric acid or a mixture thereof. Silicate electrodeposition as described in U.S. Pat. No. 3,658,662 is also effective as a means for rendering an aluminum plate hydrophilic. Another preferred aluminum plate is described in British Pat. No. 1,208,224 wherein an aluminum plate is first electrolyzed with alternating current in an electrolyte composed of hydrochloric acid and is then anodized in an electrolyte composed of sulfuric acid. The aluminum plate anodized in the method described above may be provided with a subbing layer of a cellulosic resin containing a water-soluble salt of a metal such as zinc, as described in U.S. Pat. No. 3,860,426. The subbing layer is effective in preventing the formation of scum during printing operations.

The non-silver photosensitive layer which is to be provided on such a support and which is capable of providing an oleophilic image includes those widely used in a photosensitive lithographic printing plate precursor (also known as a presensitized plate or PS plate in short). The term "oleophilicity", associated with the above-mentioned oleophilic image, refers to a high affinity to oil-based printing ink in preference to the moistening water, which, therefore, is repelled from such image areas during printing operation. Various compositions that can constitute such a photosensitive layer are well known in the art and are described in detail in published British Patent Application No. GB 2,030,309 A.

In a particularly preferred mode of this invention, a photosensitive silver halide emulsion layer is disposed on a non-silver photosensitive layer made of the composition described above and fine particles of a substantially water-insoluble lipophilic resin are dispersed in said silver halide emulsion layer. A "lipophilic resin" is such that when a coating thereof is applied to a support in a thickness of about 2 microns or more (the coated support is referred to as a specimen), the surface of the resin layer forms a substantially positive angle of contact with the support. As described by Arther W. Adamson in *Physical Chemistry of Surfaces*, Third Edition (1967), John Wiley & Sons, the angle of contact is defined as $\theta = -[\theta o/w - \theta w/o]$ wherein $\theta o/w$ is the angle of contact of kerosine in water as measured with a goniometer by the "captive bubble method" wherein fine particles (bubbles) of kerosine are brought into contact with the surface of the specimen immersed in water at 24° C., and $\theta w/o$ is the angle of contact of water in kerosine as measured with a goniometer likewise bringing fine particles (bubbles) of water into contact with the surface of the specimen immersed in kerosine. Examples of such substantially water-insoluble lipophilic resins are those which were mentioned as materials for the binder to be used in the non-silver photosensitive layer described above; for instance, shellac, polyamide resins, phenolic resins, polyvinyl acetal resins, linear polyurethane resins, phenolic novolak resins and polyester resins can be used. Besides these resins, polyvinyl cinnamate resins and photosensitive polymers such as photosensitive polyester can also be used.

The silver halide emulsion used in the present invention contains silver halide grains not exceeding 0.7 micron in grain size, which can be measured by averaging arithmetically or geometrically the projection areas of such grains by means of electron microscope. As for making such a measurement, see *The Theory of the Photographic Process*, by C. E. K. Mees and T. H. James, 3rd Edition, pp. 36–43 (Macmillan Co., 1966). Preferably, the average grain size should not exceed 0.5 micron, and more preferably should fall within the range of from 0.1 to 0.4 micron.

The silver halide emulsion used for the present invention contains a compound represented by the aforementioned formula (I). Although descriptions are found about such compounds in Japanese Patent Application (OPI) Nos. 16623/78, 66731/78, 66732/78, 49429/78, and 84714/78, U.S. Pat. No. 2,419,975, etc., such descriptions do not suggest the use thereof in accordance with the present invention, nor the advantageous features associated with its use in the present invention, since the purposes and applications of concern in the cited patents are quite different.

In formula (I), $R^1$ represents an aryl group, exemplified by substituted or unsubstituted, single- or double-ring structured aryl moieties, in which the substituent includes alkyl groups having from 1 to 20 carbon atoms, aralkyl groups having from 7 to 20 carbon atoms, alkoxy groups having from 1 to 20 carbon atoms, aryl groups substituted with mono- or di-substituted amino groups, aliphatic acylamino groups or aromatic acylamino groups. $R^2$ represents hydrogen, an aryl group, or an aliphatic group. Particularly preferred groups include a phenyl group unsubstituted or substituted with an electron attractive moiety such as a halogen atom, cyano, trifluoromethyl, carboxyl, sulfo, etc., and an unsubstituted or substituted alkyl group.

Specific examples for the group represented by $R^1$ include phenyl, α-naphthyl, β-naphthyl, p-tolyl, m-tolyl, o-tolyl, p-methoxyphenyl, m-methoxyphenyl, p-dimethylaminophenyl, p-diethylaminophenyl, p-(acetylamino)phenyl, p-(heptylamino)phenyl, p-(benzoylamino)phenyl, p-benzylphenyl, etc.

Examples of the group represented by $R^2$, in addition to hydrogen, include methyl, ethyl, n-propyl, isopropyl, phenyl, 4-chlorophenyl, 4-bromophenyl, 3-chlorophenyl, 4-cyanophenyl, 4-carboxyphenyl, 4-sulfophenyl, 3,5-dichlorophenyl, and 2,5-dichlorophenyl.

Specifically suited substituents represented by $R^1$ are single ring aryl moieties, among which the most typical ones are phenyl and tolyl.

Among the various substituents represented by $R^2$, those preferred for the present invention include hydrogen and methyl and phenyl groups, including substituted phenyl groups. The most preferred is hydrogen.

Among the compounds represented by formula (I), particularly preferred compounds can be represented by the formula (Ia)

$$R^1NHNHCOR^{12} \qquad (Ia)$$

wherein $R^1$ has the same meaning as in formula (I), while $R^{12}$ represents hydrogen, a methyl group, an unsubstituted phenyl group, or a phenyl group having an electron attractive substituent.

Among compounds represented by formula (Ia), those most preferred can be represented by the formula (Ib)

$$R^{11}NHNHCHO \qquad (Ib)$$

wherein $R^{11}$ represents unsubstituted phenyl, p-tolyl or m-tolyl.

In the following, practical examples of the compounds represented by formula (I) include

 (I-1)

 (I-2)

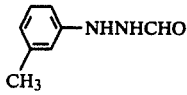 (I-3)

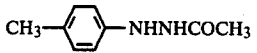 (I-4)

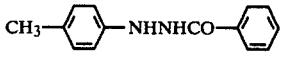 (I-5)

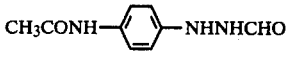 (I-6)

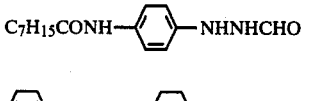 (I-7)

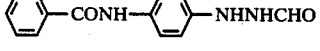 (I-8)

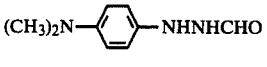 (I-9)

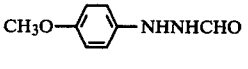 (I-10)

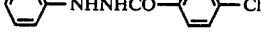 (I-11)

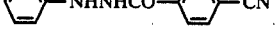 (I-12)

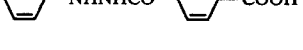 (I-13)

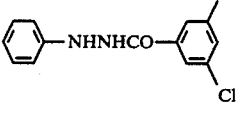 (I-14)

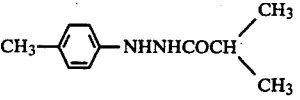 (I-15)

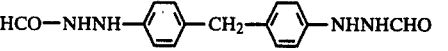 (I-16)

The compounds represented by formula (I) can be synthesized via a reaction of a hydrazine compound with formic acid or via a reaction of a hydrazine compound with an acyl halide.

Examples of synthetic methods of preparation are shown in detail below.

SYNTHESIS OF COMPOUND (2)

107 g of p-tolylhydrazine was slowly added into 110 g formic acid maintained at 25°–30° C. while stirring. After the addition was completed, another 20 minutes agitation was continued at 50° C. Upon ice cooling of the reaction system, a crystalline product separated, which was filtered and then recrystallized from 550 ml acetonitrile. The yield of colorless needle-shaped crystals was 54.5 g. Melting Point 176°–177° C.

SYNTHESIS OF COMPOUND (5)

15 g p-tolylhydrazine was added into 100 ml acetonitrile maintained at 25°–30° C. while stirring. Then 15 g benzoylchloride is added slowly and dropwise at the same temperature. After the completion of the addition, stirring was continued for 6 hours at 25°–30° C. Crystals appearing upon ice cooling were collected by filtration, and recrystallized from benzene, to obtain 7 g of colorless needle-shaped crystals having a melting point of 146° C.

The compound represented by formula (I) should preferably be present in the photographic emulsion of the present invention at a coverage of from $10^{-4}$ to $10^{-1}$ mol/mol Ag (i.e., silver present in the form of silver halide), more preferably from $10^{-3}$ to $5\times10^{-2}$ mol/mol Ag, and most preferably from $5\times10^{-3}$ to $5\times10^{-2}$ mol/mol Ag. In order to incorporate the compound of formula (I) into the emulsion, one can adopt any conventionally known method for incorporation of additives into a photographic emulsion. For example, a water-soluble compound can be added in the form of aqueous solution of an appropriate concentration, while, on the other hand, compounds insoluble or sparingly soluble in water can be added in the form of a solution of an organic solvent such as alcohol, ether, glycol, acetone, ester, amide, etc., which is water-miscible and exhibits no harmful effect on photographic properties. Those methods which are used in the case of incorporation of oil-soluble (water-insoluble) couplers into the emulsion in the form of dispersion may also be applied for the purpose of incorporating a compound according to formula (I). As a preferred embodiment, a poly(ethylene oxide) compound can be used together with the compound according to formula (I).

The poly(alkylene oxide) compounds or their derivatives for use in the present invention should preferably have molecular weights of at least 600; said poly(alkylene oxide) can be present either in the silver halide emulsion coating or in the first developer.

The poly(alkylene oxide) compound used in the present invention includes such poly(alkylene oxide) that comprises at least one units of alkylene oxide containing from 2 to 4 carbon atoms, exemplified by ethylene oxide, propylene-1,2-oxide, butylene-1,2-oxide, etc. Among these, the most preferable unit is ethylene oxide. The poly(alkylene oxide) compound further includes condensation products of the above-cited poly(alkylene oxide) with a compound having at least one active hydrogen atom such as water, aliphatic alcohol, aromatic alcohol, aliphatic carboxylic acid, organic amine, hexytol derivative, etc., and block copolymers of two or more different poly(alkylene oxide)s.

Useful embodiments of the polyalkylene oxide compounds include: p0 poly(alkylene glycol)
poly(alkylene glycol) alkyl ether
poly(alkylene glycol) aryl ether
poly(alkylene glycol) alkyl aryl ether
poly(alkylene glycol) ester
poly(alkylene glycol) aliphatic amide
poly(alkylene glycol) amine
poly(alkylene glycol) block copolymer
poly(alkylene glycol) graft copolymer More than one poly(alkylene oxide) chain can be present in a poly(alkylene oxide) molecule, provided that the total number of alkylene oxide units in the molecule is at least 10, although each individual chain length may be less than 10. Two or more poly(alkylene oxide) chains in one molecule may comprise common or different alkylene oxide units such as ethylene oxide and propylene oxide. The poly(alkylene oxide) for use in the present invention preferably contains from 14 to 100 alkylene oxide units.

Examples of poly(alkylene oxide) compounds for use in the present invention are illustrated below:

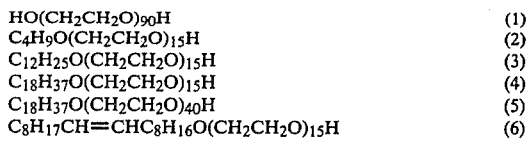

| | |
|---|---|
| $HO(CH_2CH_2O)_{90}H$ | (1) |
| $C_4H_9O(CH_2CH_2O)_{15}H$ | (2) |
| $C_{12}H_{25}O(CH_2CH_2O)_{15}H$ | (3) |
| $C_{18}H_{37}O(CH_2CH_2O)_{15}H$ | (4) |
| $C_{18}H_{37}O(CH_2CH_2O)_{40}H$ | (5) |
| $C_8H_{17}CH=CHC_8H_{16}O(CH_2CH_2O)_{15}H$ | (6) |

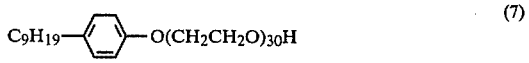

(7)

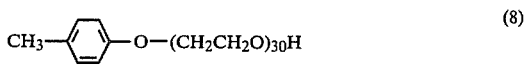

(8)

(9)

| | |
|---|---|
| $C_{11}H_{23}COO(CH_2CH_2O)_{80}H$ | (10) |
| $C_{11}H_{23}COO(CH_2CH_2O)_{24}OCC_{11}H_{23}$ | (11) |

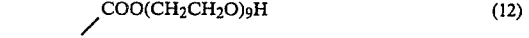

(12)

$C_{11}H_{23}CONH(CH_2CH_2O)_{15}H$ (13)

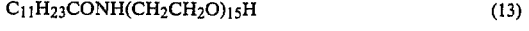

(14)

$C_{14}H_{29}N(CH_3)(CH_2CH_2O)_{24}H$ (15)

(16)

$H(CH_2CH_2O)_a(CHCH_2O)_b(CH_2CH_2O)_cH$ (17)
         |
         $CH_3$ a + b + c = 50 (an average value)
b: a + c = 10:9

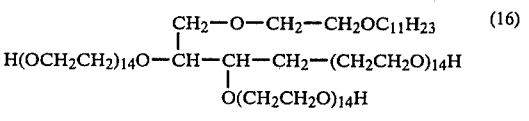

(18)

a = 50 (an average value)

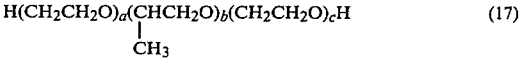

(19)

a = 50 (an average value)

$HO(CH_2CH_2O)_a(CH_2CH_2CH_2CH_2O)_b(CH_2CH_2O)_cH$ (20)
a + c = 30, b = 14

$HO(CH_2CH_2O)_a(CHCH_2O)_b(CH_2CH_2O)_cH$ (21)

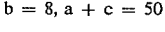

b = 8, a + c = 50

Furthermore, poly(alkylene oxide) compounds such as those set forth in Japanese Patent Application (OPI) No. 156423/75 and Japanese Patent Application Nos. 76741/76 and 24783/76 can be used. Such compounds may be used individually or in combinations thereof.

When the poly(alkylene oxide) compound is incorporated in the silver halide emulsion, the compound is dissolved in water or in a water-miscible organic solvent with a low boiling point, and the resulting solution is added to the emulsion at an appropriate manufacturing step, preferably after chemical ripening. Instead of adding it into the emulsion layer, the poly(alkylene oxide) compound can be incorporated into other, non-light-sensitive, hydrophilic colloid layers, for example, an intermediate, protective or filter layer.

The above-cited poly(alkylene oxide) compound can be present in the developer, in which case the compound may be added to the developer in the form of a solid, or in the form of a solution of an aqueous or an organic, water-miscible solvent with a suitable concentration.

The suitable concentration range for the poly(alkylene oxide) compound is from $5 \times 10^{-4}$ to 5 g per mol Ag, and more preferably from $1 \times 10^{-3}$ to 1 g per mol Ag.

Silver halide used for the present invention includes silver bromide, silver chlorobromide, mixed silver halide in which silver iodide is contained in a proportion of not higher than 10 mol%.

The photographic emulsion used in the present invention can be prepared by any one of the methods described in the following related publications: P. Glafkides, *Chimie et Physique Photographique*, (published by Paul Montel, Ltd., 1967), G. F. Duffin, *Photographic Emulsion Chemistry*, (published by the Focal Press, 1966), V. L. Zelikman et al., *Making and Coating Photographic Emulsions*, (published by the Focal Press, 1964). Such methods include single- and double-jet techniques, which classified in regard to the mixing of a soluble silver salt with a soluble halide to give rise to any type of emulsions such as acid, neutral or ammoniacal one. The combination of single- and double-jet methods is also possible.

The silver halide grains can be precipitated under the condition of silver ion excess, which is customarily called reverse mixing. As one form of double-jet method, the so-called controlled double-jet method is also applicable to the present invention, wherein the value of pAg of the phase to form silver halide is kept constant so as to produce silver halide grains with a higher order of crystallinity and better uniformity of grain size distribution.

Although a relatively wide grain size distribution is permissible for the silver halide grains involved in the photographic emulsion for the present invention, narrower distributions are preferred. In particular, distributions are preferred such that about 90% by number of the total number of silver halide grains fall within a range of ±40% of the average grain size; such emulsions are denoted as monodisperse.

The silver halide grains in the photographic emulsion can be either of regular crystalline shape, such as cubic or octahedral, or be of irregular shape, such as spherical or sheet-formed. Mixtures of these two types can be used, or the shapes may be of a combined nature of the above-cited crystalline forms.

Each silver halide grain may have different phases in its internal and surface parts, or may be homogeneous therethrough.

During grain formation or physical ripening of the silver halide grains, simple or complex salts of Cd, Zn, Pb, Tl, Ir, Rh or Fe can be added thereto.

Furthermore, various kinds of silver halide emulsions can be blended, each having been separately prepared.

Usually, water-soluble salts are removed from the emulsion after the grain formation or after physical ripening thereof by the conventionally known noodle washing in which the gelatin is gelled, or by flocculation method by use of flocculating agent such as inorganic salt containing polyvalent anion (e.g., sodium sulfate), anionic surfactant, anionic polymer (e.g., polystyrenesulfonic acid), or gelatin derivative (e.g., aliphatic acylated gelatin, aromatic acylated gelatin, aromatic carbamoyl gelatin, etc.), etc. Removal of water-soluble inorganic salts may be omitted, if desired.

The silver halide emulsion is ordinarily chemically sensitized, though one can use the so-called primitive (not after-ripened) emulsion in special cases.

For chemical sensitization, a sulfur sensitizing method may be employed, based on compounds containing sulfur capable of reacting with silver ion or on active gelatin; reducing sensitizing methods using reducing compounds, noble metal sensitizing method using noble metal compounds of other than gold, etc., may also be used, separately or in combination.

Reference can be made for these sensitizing methods to the aforementioned literatures authored by Glafkides and Zelikman, and *Die Gundlagen der Photographischen Prozesse mit Silberhalogeniden*, edited by H. Frieser and published by Akademische Verlagsgesellschaft, 1968. Sulfur sensitizing agents include thiosulfates, thiourea compounds, thiazoles, rhodanines, etc., exemplified by those described in U.S. Pat. Nos. 1,574,944, 2,410,689, 2,278,947, 2,728,668 and 3,656,955. Reducing sensitizers include stannous salts, amine compounds, formamidinesulfinic acid, silane derivatives, etc., exemplified by those described in U.S. Pat. Nos. 2,487,850, 2,518,698, 2,983,609, 2,983,610, and 2,694,637. For the purpose of noble metal sensitization, complex salts of the metals belonging to Group VIII of the Periodic Table such as Pt, Ir, Pd, etc., are used, with examples thereof described in U.S. Pat. No. 2,448,060 and British Pat. No. 618,061, etc.

The silver halide emulsion used in the present invention can contain an anti-fogging agent to achieve the objects of the invention. Suitable agents include, for example, a 1,2,3-triazole compound, a 1,2,4-triazole compound bearing a mercapto substituent at site 3, mercaptobenzimidazole compound (provided that it does not involve nitro moiety), 2-mercaptopyrimidine compound, 2-mercaptobenzothiazole compound, benzothiazolium compound (e.g., N-alkylbenzothizolium halide, N-allylbenzothiazolium halide, etc.), 2-mercapto-1,3,4-thiadiazole compound, etc. Some kinds of antifoggants, such as, for example, 6-nitrobenzimidazole, 6-hydroxy-1,3,3a,7-tetrazaindene compound, 6-mercapto-1,3,3a,7-tetrazaindene compound, etc., cannot be used alone but can be used in combination with other more preferable anti-foggants.

Anti-foggants particularly suited for the present invention are benzotriazole derivatives, in which the benzene ring may be substituted with one or more of the following moieties; an alkyl group (e.g., methyl, heptyl, etc.), a halogen atom (e.g., chlorine, or bromine), an alkoxy group (e.g., acetyl or benzoyl), an acylamino group (e.g., acetylamino, capryloylamino, benzoylamino, benzenesulfonylamino, etc.), a carbamoyl group (e.g., methylcarbamoyl, or phenylcarbamoyl), a sulfamoyl group (e.g., methylsulfamoyl, phenylsulfamoyl, etc.), an aryl group (e.g., phenyl or tolyl), etc. Such an alkyl substituent should preferably have carbon atoms not exceeding 12 and more preferably 3 or less. The 1-position of the benzotriazole may be substituted with a halogen atom such as chlorine or bromine.

The advantageous features of the present invention are enhanced by the addition of a small amount (preferably $10^{-4}$ to $10^{-2}$ mol/mol Ag) of iodide such as potassium iodide to the emulsion after the grain formation and either before or after chemical ripening prior to coating.

The photographic emulsion of the present invention can be spectrally sensitized with various types of dyes, including methine dyes. Suitable types of dyes include cyanine, merocyanine, complex cyanine, complex merocyanine, holopolar cyanine, hemicyanine, styryl, and hemioxonol, among which cyanine, merocyanine and complex merocyanine dyes are particularly useful. These dyes can advantageously contain any one of heterocyclic nuclei of basic nature known as nuclei of ordinary cyanine dyes. Such nuclei include pyrrole, oxazoline, thiazoline, pyrroline, oxazole, thiazole, selenazole, imidazole, tetrazole, pyridine, etc., those consisting of any one of the above-cited nuclei fused with an aliphatic hydrocarbon ring structure, those consisting of any one of the above-cited nuclei fused with an aromatic hydrocarbon ring structure, exemplified by indolenine, benzindolenine, indole, benzoxazole, naphthoxazole, benzothiazole, naphthothiazole, benzoselenazole, benzimidazole, quinoline, etc. These nuclei can be substituted with known photographically suitable moieties at their carbon sites.

Merocyanine or complex merocyanine dyes can contain a ketomethylene nucleus exemplified by the following 5- or 6-membered heterocyclic rings: pyrazoline-5-one, thiohydantoin, 2-thioxazolidine-2,4-dione, thiazolidine-2,4-dione, rhodanine, thiobarbituric acid, etc.

Suitable dye sensitizers are disclosed in the following patents: German Pat. No. 929,080, U.S. Pat. Nos. 2,231,658, 2,493,748, 2,503,776, 2,519,001, 2,912,329, 3,656,959, 3,672,897 and 3,694,217, British Pat. No. 1,242,588 and Japanese Patent Publication No. 14030/69.

Although the dye sensitizers cited above can be used individually, they can further be used in combination, particularly for the purpose of supersensitization. Such techniques are described, for example, in U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,813,609 and 3,837,862, British Pat. No. 1,344,281, and Japanese Patent Publication No. 4936/68.

In addition to the spectral sensitizer, a substance which, although lacking in spectral sensitizing capability by itself indifferent to its absorption in the visible region of the spectrum, can exhibit a supersensitizing ability can be used. Such a substance is exemplified by aminostilbene compounds having a nitrogen-containing heterocyclic ring as substituent (those set forth in, for example, U.S. Pat. Nos. 2,933,390 and 3,635,721), aromatic carboxylic acid/formaldehyde condensation products (those described in U.S. Pat. No. 3,743,510), cadmium salts, azaindene compounds, etc. Combinations of ingredients set forth in U.S. Pat. Nos. 3,615,613, 3,615,641, 3,617,295 and 3,635,721 are specifically useful.

The photographic emulsion used in the present invention can include water-soluble dyes therein with various purposes including light filtration, prevention of irradiation, etc. Suitable types of dye include oxonol, hemioxonol, styryl, merocyanine, cyanine, and ozo. Among these, oxonol, hemioxonol and merocyanine types of dye are particularly advantageous. Practical examples of such dyes are described in the following patents: British Pat. Nos. 584,609 and 1,177,429, Japanese Patent Application (OPI) Nos. 85130/73, 99620/74, and 114420/74, and U.S. Pat. Nos. 2,274,782, 2,533,472, 2,956,879, 3,148,187, 3,177,078, 3,247,127, 3,540,887, 3,575,704, 3,653,905 and 3,718,472.

The photographic emulsion used in the present invention can contain inorganic or organic hardening agents such as chromium salt (e.g., chromium alum, chromium acetate, etc.), aldehyde (formaldehyde, glyoxal, glutaraldehyde, etc.), N-methylol compound (e.g., dimethylolurea, methyloldimethylhydantoin, etc.), dioxane derivative (2,3-dihydroxydioxane, etc.), active vinyl compound (e.g., 1,3,5-triacryloyl-hexahydro-s-triazine, bis(vinylsulfonyl)methyl ether, etc.), active halogen compound (e.g., 2,4-dichloro-6-hydroxy-s-triazine, etc.), mucochloric acid and other mucohalogen acids (mucophenoxychloric acid, etc.), isoxazole, dialdehyde starch, 2-chloro-6-hydroxytriazinylated gelatin, etc. They may be used individually or in combination. Practical examples of such compounds are found in U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,644 and 3,543,292, British Pat. Nos. 676,628, 825,544 and 1,270,578, German Pat. Nos. 872,153 and 1,090,427, Japanese Patent Publication Nos. 7133/59 and 1872/71, etc.

The photographic emulsion used in the present invention can further contain conventionally known types of surfactant for the purposes of coating aids, static prevention, improvement of slipping property, emulsification, anti-blocking, and photographic performance improvement (e.g., acceleration of development, contrast increase, sensitization, etc.), etc.

Suitable surface active agents include the following: Nonionic surfactants: saponin (steroid derivative), alkylene oxide derivatives (e.g., polyethylene glycol, polyethylene glycol/polypropylene glycol condensate, polyethylene glycol alkyl or aryl ether, polyethylene glycol ester, polyethylene glycol sorbitan ester, polyalkylene glycol alkylamine or amide, silicone compounds attached with polyethylene oxide, etc., glycidol derivative (e.g., alkenylsuccinic acid polyglyceride, alkylphenol polyglyceride, etc.), the aliphatic acid ester of polyhydric alcohol, and other alkyl esters, urethane or ether thereof.

Anionic surfactants: saponins of the triterpenoid family, salts of alkylcarboxylic acids, salts of alkylsulfonic acids, salts of alkylbenzenesulfonic acids, salts of alkylnaphthalenesulfonic acids, alkylsulfonic acid esters, alkylphosphonic acid ester, N-acyl-N-alkyltaurines, sulfosuccinic acid esters, sulfoalkylpolyoxyethylene alkylphenol ethers, polyoxyethylene alkylphosphoric acid esters, etc., which compounds all contain acid moieties such as carboxyl, sulfo, phospho, sulfuric acid ester, phosphoric acid ester, etc.

Amphoteric surfactants: amino acids, aminoalkylsulfonic acids, aminoalkylsulfonic or phosphoric acid esters, alkylbetaines, amine imides, amine oxides, etc. Cationic surfactants: alkylamine salts, pyridinium imidazolium and other heterocyclic quaternary ammonium salts, sulfonium or phosphonium salts containing aliphatic or heterocyclic groups, etc.

Related descriptions on surface active agent are found in U.S. Pat. Nos. 2,240,472, 2,831,766, 3,158,484, 3,210,191, 3,294,540 and 3,507,660, British Pat. Nos. 1,012,495, 1,022,878, 1,179,290 and 1,198,450, Japanese Patent Application (OPI) No. 117414/75, U.S. Pat. Nos. 2,739,891, 2,823,123, 3,068,101, 3,415,649, 3,666,478 and 3,756,828, British Pat. No. 1,397,218, U.S. Pat. Nos. 3,133,816, 3,441,413, 3,475,174, 3,545,974, 3,726,683 and 3,843,368, Belgian Pat. No. 731,126, British Pat. Nos. 1,138,514, 1,159,825 and 1,374,780, Japanese Patent Publication Nos. 378/65, 379/65 and 13822/68, U.S. Pat. Nos. 2,271,623, 2,288,226, 2,944,900, 3,253,919, 3,671,247, 3,772,021, 3,589,906, 3,666,478 and 3,754,924, German Patent Application (OLS) No. 1,961,638, Japanese Patent Application (OPI) No. 59025/75, etc.

As the binder or protective colloid for the photographic emulsion, gelatin is most advantageously used, but other hydrophilic colloid materials can also be used, including gelatin derivatives, graft copolymers consisting of gelatin and other high polymers, proteins such as albumin, casein, etc., cellulose derivatives such as hydroxyethyl celluose, carboxymethyl cellulose, cellulose sulfate, etc., carbohydrate derivatives such as sodium alginate, starch derivatives, etc., synthetic hydrophilic polymers such as poly(vinyl alcohol), partially acetalized poly(vinyl alcohol), poly-N-vinylpyrrolidone, poly(acrylic acid), poly(methacrylic acid), polyacrylamide, polyvinylimidazole, polyvinylpyrazole, etc.

Among various types of gelatin that can be used, in addition to lime-processed one, acid-processed gelatin as well as the hydrolyzed product and enzyme-decomposition product of gelatin can be used. Gelatin derivatives can be prepared by treating gelatin with a variety of reactive species such as, for example, acid halide, acid anhydride, isocyanate, bromoacetic acid, alkane sultone, vinylsulfonamide, maleimide, poly(alkylene oxide), epoxide, etc. Specific descriptions about the techniques therefor are found, for example, in U.S. Pat. Nos. 2,614,928, 3,132,945, 3,186,846 and 3,312,553, British Pat. Nos. 861,414, 1,033,189 and 1,005,784, Japanese Patent Publication No. 26845/67.

Graft polymers containing gelatin can have as the monomer unit for the synthetic grafted part acrylic acid, methacrylic acid, esters or amides of these two acids, acrylonitrile, styrene and other vinyl monomers. Particularly such graft compositions are preferred which exhibit a comparatively high degree of compatibility with gelatin, including polymer chains comprising acrylic and methacrylic acid, acrylamide, methacrylamide, hydroxyalkyl methacrylate, etc. See, for example, U.S. Pat. Nos. 2,763,625, 2,831,767 and 2,956,884, etc. Typical hydrophilic polymers of synthetic origin include those described in German Patent Application (OLS) No. 2,312,708, U.S. Pat. Nos. 3,620,751 and 3,879,205 and Japanese Patent Publication No. 7561/68.

The non-silver photosensitive layer and the silver halide emulsion coating for use in the instant invention can be prepared by, for example, dip coating, air knife coating, curtain flow coating, extrusion coating, hopper coating, etc. The coating coverage of the light-sensitive silver halide photographic emulsion, on a dry basis is, preferably, from 1 to 10 g/m$^2$; higher values tend to deteriorate image reproducibility. What is more important is the coating coverage of silver, the preferred range of which is from 9 to 33 mmol/m$^2$ (millimols/meter$^2$), and more preferably from 12 to 20 mmol/m$^2$ for the present purposes. These values are less than those for the conventional lith film (50–70 mmol/m$^2$), thus realizing silver saving. Too much amount of silver increases contrast, but promotes unfavorable growth of image areas. Edge sharpness of image is reduced with lesser amounts of silver. It should be emphasized that a high contrast gradation is not necessarily associated with the improvement of image quality but that, under a proper condition of contrast, the above-cited ranges for coating coverage as well as for silver amount prominent features characterizing the present invention are exhibited.

The first developer used in the present invention should preferably contain dissociated sulfite ion at a concentration of at least 0.18 mol/l and substantially a dihydroxybenzene compound alone as the principal reducing agent. The concentration of dissociated sulfite ion should more preferably be not less than 0.25 mol/l. Dihydroxybenzene compounds for reducing agent include, for example, hydroquinone, chlorohydroquinone, bromohydroquinone, isopropylhydroquinone, methylhydroquinone, 2,3-dichlorohydroquinone, 2,5-dimethylhydroquinone, etc. Among these, hydroquinone is preferred. The above-cited compounds may be used individually or in combination. The principal reducing agent is favorably contained in the developer at a coverage of from 2 to 80 g/l and more favorably from 5 to 60 g/l.

Though the first developer of the present invention substantially contains dihydroxybenzene compounds alone as reducing agent, a limited amount of an auxiliary reducing agent such as 1-phenyl-3-pyrazolidone, derivatives thereof, N-methyl-p-aminophenol and its derivative, etc., can be present with a deep care of not using such an excessive amount as to prevent the realization of the purposes of the present invention represented by the improvement of dot image quality.

The developer can further include other conventionally known additives such as preservative, alkaline agent, pH buffer, anti-foggant, etc. Furthermore, the following ingredients may be added, if desired: organic solvent, tint controlling agent, development accelerator, surfactant, anti-foamer, softener for hard water, hardening agent, viscosity controlling agent, etc.

As one modified embodiment of the present invention, one can incorporate the principal reducing agent of dihydroxybenzene compound in the silver halide photographic emulsion coating and employs a first developer not containing the reducing agent, though, of course, it is more preferable for the reducing agent to be present in the developer.

In order to achieve image fix in the instant invention, ordinary compositions for fixing fluid well known to those skilled in the art can be applied. Suitable fixing agents include thiosulfate salts, thiocyanate salts; organic acids such as glacial acetic acid or citric acid, and organic sulfur compounds can be used as fixation promotor. Wash-off of the emulsion coating can be performed by the use of hot water or a solution containing protein-decomposing enzyme as is set forth in Japanese Patent Application No. 100596/79.

To perform the second development of the non-silver photosensitive layer, one can employ any type of developer conventionally used in the processing of the ordinary PS plates. Exemplary are the aqueous solution of sodium silicate for PS layers comprising an o-quinonediazide compound, and those set forth in U.S. Pat. No. 4,141,733.

Preparation of a lithographic printing plate from a photosensitive plate produced in accordance with the present invention can be carried out via the following processing steps. First of all, a latent image is formed in the silver halide grains in the photographic emulsion coating by imagewise exposure. Then, a first development is carried out to develop the exposed silver halide grains. By a subsequent fixing, an image comprising silver is obtained. Using the thus-formed silver image as a mask, uniform radiation of light active to the underlying non-silver photosensitive layer is provided. After removal of the silver halide emulsion coating by wash-off, the second development is performed to remove either the exposed or the unexposed area of the layer whereby the hydrophilic surface of the support is exposed to give rise to a printing plate.

At the image exposure, a projection lens system or a scanning exposure system is used with a magnification ratio of from 1:10 to 10:1. As regards the first development, the suitable range for the temperature is from 20° C. to 50° C., and more preferably from 24° C. to 40° C., while the processing time is from 10 to 120 seconds, and more preferably from 10 to 40 seconds. Fixing can generally be performed for from 1 to 30 seconds, and more preferably from 1 to 10 seconds. The blanket radiation for the non-silver photosensitive layer is not longer than 30 seconds. Wash-off of the emulsion is carried out at a temperature ranging from ambient to 60° C., and more preferably from 35° to 45° C., for from 10 to 60 seconds, and more preferably for from 10 to 30 seconds. The second development conditions are room temperature to 50° C., and more preferably up to 40° C. for processing temperature and duration of 10 to 120, and more preferably of from 10 to 45 seconds. Finally, gum coating can be carried out according to the conventional manner. These processings may be performed with automatic processors.

In the following, the present invention will be explained more in detail describing some practical examples, in which % means always by weight if not otherwise designated.

EXAMPLE 1

The surface of a 2S grade aluminum sheet which had been mechanically grained is fractionally etched by being immersed in a 2% sodium hydroxide aqueous solution maintaining at 40° C. for 1 minute. After rinsed with water, the sheet was immersed in a mixture of sulfuric acid and chromic acid for about 1 minute to expose a clean aluminum surface. Then the sheet was subjected to anodizing in a 20% sulfuric acid bath maintained at 30° C. while applying d.c. voltage of 1.5 volts and current density of 3 A/dm$^2$ for 2 minutes. After a water rinse and drying of the sheet, a photosensitive coating mixture of the following composition was coated on the sheet by means of roll coating so as to provide a coating weight of 2 g/m$^2$ (dry basis). Thus, the non-silver photosensitive layer was prepared.

| | |
|---|---|
| The naphthoquinone-1,2-diazide(2)-5-sulfonic acid ester of an acetone-pyrogallol resins (synthesized by the method set forth in Example 1 of U.S. Pat. No. 3,635,709) | 2.5 g |
| Hitanol #3110 (a cresol-formaldehyde resin available from Hitachi Chemical Ind.) | 5.0 g |
| Methyl ethyl ketone | 75 g |
| Cyclohexanone | 60 g |

Separately, silver iodobromide emulsion A was prepared as follows. To an aqueous gelatin solution maintained at 50° C., an aqueous silver nitrate solution and an aqueous potassium bromide solution were simultaneously added, while stirring for 50 minutes during which time the pAg value of the whole system was adjusted to 7.9, to obtain a silver bromide emulsion containing 0.25 micron (on average) grains. After removal of the water-soluble salts by an ordinary process, the emulsion was chemically ripened with the addition of 43 mg sodium thiosulfate per 1 mol silver bromide at 60° C. for 1 hour. Finally the 0.4 mol% equivalent amount of potassium iodide was incorporated to provide silver iodobromide emulsion A. In this emulsion, 70 g of gelatin was present per mol of silver iodobromide, and 0.85 mol of silver iodobromide was present per kg of the emulsion.

To 2 kg of this silver iodobromide emulsion A, various amounts of Compound I-2 and 6-methylbenzotriazole were added, as shown in Table 1.

Then, the photosensitive emulsion mixture of the following composition was continuously coated so as to give a coating weight of 4.5 g/m$^2$ after drying with the hot air of the highest temperature of 110° C. The resulting sample is designated No. 1.

| Composition of the photosensitive emulsion mixture | |
|---|---|
| An emulsified dispersion obtained by dispersing a solution of 45 g MP120HH (A phenol-formaldehyde resin produced by Gun-ei Chemical Ind.) in a mixture of 330 g ethyl acetate and 120 g methyl ethyl ketone into a mixture comprising 600 ml of a 10% aqueous gelatin solution, 60 ml of a 10% aqueous solution of sodium nonylbenzenesulfonate and 150 ml of a 10% methanol solution of turkey-red oil | 1,300 g |
| A 0.1% methanol solution of the sodium salt of 1,3-diethyl-5-{2-[3 -(3-sulfopropyl)benzoxazole-2-ylidene]ethylidene}-thiohydantoin | 100 ml |
| A 0.5% aqueous alkaline solution of 4-hydroxy-6-methyl-1,3,3a,7-tetrazaindene | 200 ml |
| A 2% aqueous solution of 2,4-dichloro-6-hydroxy-s-triazine | 70 ml |

All of the above-listed components were added to emulsion A to give the coating mixture, which was overcoated on the non-silver photosensitive layer continuously and subjected to drying with hot air with the final temperature of 110° C.

TABLE 1

| Sample No. | Amount of Compound I-2 Added (g) | Amount of 6-Methyl-benzotriazole Added (g) | Coating Density of Silver (mmol/m$^2$) |
|---|---|---|---|
| 1 | 4.0 | 0.85 | 14 |
| 2 | 4.0 | 0 | 14 |
| A | 0 | 0 | 14 |

TABLE 1-continued

| Sample No. | Amount of Compound I-2 Added (g) | Amount of 6-Methyl-benzotriazole Added (g) | Coating Density of Silver (mmol/m²) |
|---|---|---|---|
| 3 | 4.0 | 0 | 50 |

After standing for one week, each sample was subjected to plate making as follows. An image exposure was performed with a transparent negative film obtained by photographing a reflux original containing a screened halftone image with a hot density of 100 lines/inch with a demagnification ratio of about ⅓. The negative film image was projected on the sample at a magnification ratio of about three by means of a projector provided with a 300 lux light source.

Then, the following processing was conducted in an automated processor: Developer (I) of the following composition was passed through the automatic processor at 32° C. for 30 seconds, and then through Fixing Fluid (I) at 20° C. for 10 seconds. Then, the plate was uniformly exposed by the use of 3 reflection type mercury lamps. Wash-off fluid (I) maintained at 40°-45° C. was supplied to the wash-off station. The plate was rubbed with brushes, passed through squeeze roller pairs and immersed in Developer (II) of the following composition at 30° C. for 30 seconds. Finally, a 14° Bé aqueous gum arabic solution was applied on the plate to provide a finished printing plate.

| Developer (I) | |
|---|---|
| Hemisulfate salt of N—methyl-p-aminophenol | 5 g |
| Hydroquinone | 10 g |
| Sodium sulfite (anhydrous) | 75 g |
| Sodium metaborate (bihydrate) | 30 g |
| Potassium hydroxide | 12 g |
| Water to make | 1,000 ml |
| | (pH = 11.5) |
| Developer (II) | |
| Sodium silicate, JIS grade 1 | 100 g |
| Sodium metasilicate | 50 g |
| Purified water | 1,800 ml |
| Fixing Fluid (I) | |
| Water | 700 ml |
| Ammonium thiosulfate | 224 g |
| Sodium sulfite | 20 g |
| Water to make | 1,000 ml |
| Wash-Off Fluid (I) | |
| Bioplaze PN-4 (a protein decomposing enzyme produced by Nagase Biochemical Ind.) | 5 g |
| Water to make | 1,000 ml |

Each plate was subjected to printing with use of Heidel KOR printer whereby the following results in Table 2 for printing image quality were obtained.

TABLE 2

| Sample No. | Reproducing Range for Screened Image (%) | Edge Sharpness for Text |
|---|---|---|
| 1 | 3-90 | excellent |
| 2 | 5-85 | excellent |
| a | 15-65 | poor |
| 3 | 7-80 | good |

EXAMPLE 2

The procedures described in the preceding example were precisely repeated except that the following conditions were changed to obtain Sample No. 4.

1. Silver Halide Photographic Emulsion B Used

| Silver chlorobromide/gelatin emulsion (Cl⁻ content = 70 mol %, Br⁻ content = 30 mol %, average grain size = 0.28 micron, gelatin content = 55 g per 1 kg emulsion, silver halide content = 0.85 mol per 1 kg emulsion) | 2,000 g |
|---|---|

2. Additives Used

After the addition of 4 g of Compound I-2, 0.4 g of poly(alkylene oxide) compound (18) was further added and, instead of 6-methylbenzotriazole, 5-nitroindazole was added in an amount of 1.2 g.

3. Coating Rate of Silver 20 mmol/m²

In the plate making operations, the steps described in Example 1 were repeated, except for the use of Developer (III) in the following in place of Developer (I) (used for the first development).

| Developer (III) | |
|---|---|
| Sodium salt of ethylenediamine-tetraacetic acid | 1.0 g |
| Potassium bromide | 5.0 g |
| Sodium sulfite | 75 g |
| Hydroquinone | 28 g |
| Sodium carbonate (monohydrate) | 12 g |
| Potassium hydroxide | 25 g |
| Water to make | 1,000 ml |

The first development was conducted at 32° C. for 45 seconds. Printing with Heidel KOR printer demonstrated a printing durability of the plate of about 100,000 with a start-up loss of only five. The reproducing range for screened image was from 3 to 95%, and the edge sharpness for text was excellent.

While the invention has been described in detail and with reference to specific embodiments thereof, it will be apparent to one skilled in the art that various changes and modifications can be made therein without departing from the spirit and scope thereof.

What is claimed is:

1. A photosensitive lithographic printing plate precursor comprising, in sequence, a support having a hydrophilic surface, a non-silver photosensitive layer capable of producing an oleophilic image, and a photographic silver halide emulsion coating, wherein said silver halide emulsion coating comprises silver halide grains with an average diameter not exceeding 0.7 micron and a compound represented by the formula (I)

$$R^1NHNHCOR^2 \qquad (I)$$

wherein $R^1$ represents an aryl group and $R^2$ represents hydrogen, an aryl group, or an aliphatic group.

2. A photosensitive lithographic printing plate precursor as in claim 1 wherein said silver halide emulsion coating additionally comprises a poly(alkylene oxide)

or a derivative thereof having a molecular weight of at least 600, and the coating coverage of said silver halide emulsion coating is from 1 to 10 g/m², and the silver density is from 9 mmol/m² to 33 mmol/m².

3. A method for preparing a lithographic printing plate comprising
(a) imagewise exposing a photosensitive lithographic printing plate precursor comprising, in sequence, a support having a hydrophilic surface, a non-silver photosensitive layer capable of forming an oleophilic image, and a photographic silver halide emulsion coating,
wherein said silver halide emulsion coating comprises silver halide grains with an average grain size not exceeding 0.7 micron and a compound represented by the formula (I)

$$R^1NHNHCOR^2 \qquad (I)$$

wherein $R^1$ represents an aryl group, and $R^2$ represents hydrogen, an aryl group or an aliphatic group together with a poly(alkylene oxide) or a derivative thereof having a molecular weight of at least 600,
(b) subjecting said exposed plate to a first development with a first developer containing a dihydroxybenzene reducing agent and free sulfite ions having a concentration of at least 0.18 mol/l,
(c) fixing the developed photographic coating,
(d) uniformly exposing the thus-processed plate to radiation to which said non-silver photosensitive layer is sensitive,
(e) washing to remove said silver halide emulsion coating, and
(f) processing the plate with a second developer capable of developing said non-silver photosensitive layer to remove either the exposed areas or unexposed area with the radiation of said non-silver photosensitive layer to form an oleophilic image.

4. A photosensitive lithographic printing plate precursor as in claim 1 or 2 wherein the average grain size does not exceed 0.5 micron.

5. A method for preparing a lithographic printing plate as in claim 3 wherein the average grain size does not exceed 0.5 micron.

6. A photosensitive lithographic printing plate precursor as in claim 1 or 2 wherein the average grain size is within the range of from 0.1 to 0.4 micron.

7. A method for preparing a lithographic printing plate as in claim 3 wherein the average grain size is within the range of from 0.1 to 0.4 micron.

8. A photosensitive lithographic printing plate precursor as in claim 1 or 2 wherein the compound according to formula (I) is represented by the formula (Ia)

$$R^1NHNHCOR^{12} \qquad (Ia)$$

wherein $R^1$ has the same meaning as in formula (I), and $R^{12}$ represents hydrogen, a methyl group, an unsubstituted phenyl group, or a phenyl group having an electron attractive substituent.

9. A method for preparing a lithographic printing plate as in claim 3 wherein the compound according to formula (I) is represented by the formula (Ia)

$$R^1NHNHCOR^{12} \qquad (Ia)$$

wherein $R^1$ has the same meaning as in formula (I), and $R^{12}$ represents hydrogen, a methyl group, an unsubstituted phenyl group, or a phenyl group having an electron attractive substituent.

10. A photosensitive lithographic printing plate precursor as in claim 8 wherein the compound represented by formula (I) is represented by the formula (Ib)

$$R^{11}NHNHCHO \qquad (Ib)$$

wherein $R^{11}$ represents unsubstituted phenyl, p-tolyl or m-tolyl.

11. A method for preparing a lithographic printing plate as in claim 9 wherein the compound represented by formula (I) is represented by the formula (Ib)

$$R^{11}NHNHCHO \qquad (Ib)$$

wherein $R^{11}$ represents unsubstituted phenyl, p-tolyl or m-tolyl.

12. A photosensitive lithographic printing plate precursor as in claim 1 or 2 wherein the compound represented by formula (I) is present in the silver halide emulsion at a density of from $10^{-4}$ to $10^{-1}$ mol/mol Ag.

13. A method for preparing a lithographic printing plate as in claim 3 wherein the compound represented by formula (I) is present in the silver halide emulsion at a density of from $10^{-4}$ to $10^{-1}$ mol/mol Ag.

14. A photosensitive lithographic printing plate precursor as in claim 1 or 2 wherein the compound represented by formula (I) is present in the silver halide emulsion at a density of from $10^{-3}$ to $5 \times 10^{-2}$ mol/mol Ag.

15. A method for preparing a lithographic printing plate as in claim 3 wherein the compound represented by formula (I) is present in the silver halide emulsion at a density of from $10^{-3}$ to $5 \times 10^{-2}$ mol/mol Ag.

16. A photosensitive lithographic printing plate precursor as in claim 1 or 2 wherein the compound represented by formula (I) is present in the silver halide emulsion at a density of from $5 \times 10^{-3}$ to $5 \times 10^{-2}$ mol/mol Ag.

17. A method for preparing a lithographic printing plate as in claim 3 wherein the compound represented by formula (I) is present in the silver halide emulsion at a density of from $5 \times 10^{-3}$ to $5 \times 10^{-2}$ mol/mol Ag.

18. A method for preparing a lithographic printing plate comprising
(a) imagewise exposing a photosensitive lithographic printing plate precursor comprising, in sequence, a support having a hydrophilic surface, a non-silver photosensitive layer capable of forming an oleophilic image, and a photographic silver halide emulsion coating,
wherein said silver halide emulsion coating comprises silver halide grains with an average grain size not exceeding 0.7 micron,
(b) subjecting said exposed plate to a first development with a developer containing a compound represented by the formula (I)

$$R^1NHNHCOR^2 \qquad (I)$$

wherein $R^1$ represents an aryl group, and $R^2$ represents hydrogen, an aryl group or an aliphatic group, a dihydroxybenzene reducing agent, and free sulfite ions having a concentration of at least 0.18 mol/l.,
(c) fixing the developed photographic coating, (d) uniformly exposing the thus-processed plate to radiation to which said non-silver photosensitive layer is sensitive, (e) washing to remove said silver halide emulsion coating, and (f) processing the plate with a second developer capable of developing said non-silver photosensitive layer to form an oleophilic image.

19. A photosensitive lithographic printing plate precursor as in claim 2 wherein said poly(alkylene oxide) contains from 14 to 100 alkylene oxide units.

20. A photosensitive lithographic printing plate precursor as in claim 2 wherein the concentration of poly(alkylene oxide) compound is from $5 \times 10^{-4}$ to 5 g/mol of silver halide.

21. A photosensitive lithographic printing plate precursor as in claim 2 wherein the concentration of poly(alkylene oxide) compound is from $1 \times 10^{-3}$ to 1 g/mol of silver halide.

22. A photosensitive lithographic printing plate precursor as in claim 1 or 2 wherein about 90% by number of the total number of silver halide grains fall within a range of ±40% of the average grain size.

23. A photosensitive lithographic printing plate precursor as in claim 4 wherein about 90% by number of the total number of silver halide grains fall within a range of ±40% of the average grain size.

24. A photosensitive lithographic printing plate precursor as in claim 6 wherein about 90% by number of the total number of silver halide grains fall within a range of ±40% of the average grain size.

25. A photosensitive lithographic printing plate precursor as in claim 2 wherein the silver density is from 12 mmol/m² to 20 mmol/m².

26. A method for preparing a lithographic printing plate as in claim 3 wherein the free sulfite ions have a concentration of at least 0.25 mol/l.

* * * * *